(12) United States Patent
Sekar et al.

(10) Patent No.: US 8,153,132 B2
(45) Date of Patent: Apr. 10, 2012

(54) ANTIBODIES IMMUNOREACTIVE WITH MUTANT HYDROXYPENYLPYRUVATE DIOXYGENASE

(75) Inventors: Vaithilingam Sekar, Ames, IA (US); Bruce Held, Ames, IA (US); Kyu Chung, Basil (CH); Paul F. Russell, Jr., Portage, MI (US)

(73) Assignee: MS Technologies, Inc., West Point, IA (US)

( * ) Notice: Subject to any disclaimer, the term of this patent is extended or adjusted under 35 U.S.C. 154(b) by 315 days.

(21) Appl. No.: 12/609,200

(22) Filed: Oct. 30, 2009

(65) Prior Publication Data

US 2011/0104755 A1    May 5, 2011

(51) Int. Cl.
*C12P 21/00*    (2006.01)
*C07K 16/00*    (2006.01)
*C12N 1/00*    (2006.01)
*G01N 33/53*    (2006.01)

(52) U.S. Cl. ............... 424/146.1; 424/150.1; 530/387.9; 530/389.5; 530/387.1

(58) Field of Classification Search .......................... None
See application file for complete search history.

(56) References Cited

U.S. PATENT DOCUMENTS

| | | | |
|---|---|---|---|
| 6,245,968 B1 | 6/2001 | Boudec | |
| 6,268,549 B1 | 7/2001 | Sailland et al. | |
| 7,807,791 B2 | 10/2010 | Sekar et al. | |
| 2003/0066102 A1 | 4/2003 | Maxwell et al. | |

FOREIGN PATENT DOCUMENTS

| | | |
|---|---|---|
| WO | WO9749816 A1 | 12/1997 |
| WO | WO2006072607 A2 | 7/2006 |

OTHER PUBLICATIONS

Greenspan et al. (Nature Biotechnology 17: 936-937, 1999).*
Campbell, A.M. (Monoclonal Antibody Technology, Elsevier N.Y. 1984; chapter 1, pp. 1-32).*
Lenne et al. "Localization and partial purification of P=hydroxyphenylpyruvate dioxygenase from cultured carrot cells" Photoxynthesis: from light to Biosphere. Proceedings of the International Photosynthesis Congress XX, XX, vol. 5, Aug. 20, 1995 pp. 285-288, XP000646348, p. 287.
ABBAS et al. (2000) Cellular and Molecular Immunology, 4th edition, p. 55 and 477.
Ruetschi et al. (1992) Eur. J. Biochem. 205, 459-466.
Serre et al., GenPept Accession No. PDB:1CJXA (Sep. 24, 2008).
Olivera et al., GenBank Access No. AAO12525 (May 10, 2005).
O'Hare et al., GenBank Accession No. ABC88387.2 (Jun. 8, 2006).
Durfourmantel et al., GenBank Accession No. ABF50055 (Dec. 1, 2008).
Paulsen et al. GenBank Accession No. CP000076.1 (Sep. 10, 2007).
Silby et al., GenBank Accesson No. CP000094.2 (Jul. 15, 2009).
Gill et al. NCBI Reference No. NP_745571 (Dec. 14, 2010).
Buell et al. NCBI Reference No. NP_793333 (Feb. 4, 2001).
Ruetschi et al. Swiss-Prot Ref No. P80064.1 (Feb. 9, 2011).
Feil et al. NCBI Ref No. YP_236400.1 (Feb. 4, 2011).
Gross et al. NCBI Reference No. YP_260492.1 (May 24, 2010).
Joardar et al. NCBI Reference No. YP_275410 (Feb. 3, 2011).
Silby et al. NCBI Reference No. YP_34648.1 (May 24, 2010).
Copeland et al. NCBI Reference No. YP_001267652.1 (Feb. 10, 2011).
Copeland et al. NCBI Reference No. YP_001668737.1 (Feb. 10, 2011).
Copeland et al. NCBI Reference No. YP_001749309.1 (Feb. 9, 2011).
Silby et al. NCBI Reference No. YP_002872577.1 (Feb. 14, 2011).
BLAST Basic Local Alignment Search Tool Results May 15, 2009.

* cited by examiner

*Primary Examiner* — Robert A Zeman
(74) *Attorney, Agent, or Firm* — Patricia A. Sweeney

(57) ABSTRACT

Antibodies immunoreactive to mutant *Pseudomonas* HPPD are provided, and in an embodiment the mutant HPPD is one in which the wild-type HPPD is substituted at residue 336 with tryptophan for glycine. Also provided are hybridomas producing the antibodies, as well as methods of making and using the antibodies.

4 Claims, 5 Drawing Sheets

Figure 1

```
      1 ATGAAACATCACCATCACCATCACCATATGCAG 33 (HIS-tag)
  ORF
  →
    1 atggcagatctatacgaaaacccaatgggcctgatgggctttgaa 45
      M  A  D  L  Y  E  N  P  M  G  L  M  G  F  E
   46 ttcatcgaattcgcgtcgccgacgccgggtacctggagccgatc 90
      F  I  E  F  A  S  P  T  P  G  T  L  E  P  I
   91 ttcgagatcatgggcttcaccaaagtcgcgacccaccgttccaag 135
      F  E  I  M  G  F  T  K  V  A  T  H  R  S  K
  136 aacgtgcacctgtaccgccagggcgagatcaacctgatcctcaac 180
      N  V  H  L  Y  R  Q  G  E  I  N  L  I  L  N
  181 aacgagcccaacagcatcgcctcctactttgcggccgaacacggc 225
      N  E  P  N  S  I  A  S  Y  F  A  A  E  H  G
  226 ccgtcggtgtgcggcatggcgttccgcgtgaaggactcgcaaaag 270
      P  S  V  C  G  M  A  F  R  V  K  D  S  Q  K
  271 gcctacaaccgcgccctggaactcggcgcccagccgatccatatt 315
      A  Y  N  R  A  L  E  L  G  A  Q  P  I  H  I
  316 gacaccgggccgatggaattgaacctgccggcgatcaagggcatc 360
      D  T  G  P  M  E  L  N  L  P  A  I  K  G  I
  361 ggcggcgcgccgttgtacctgatcgaccgtttcggcgaaggcagc 405
      G  G  A  P  L  Y  L  I  D  R  F  G  E  G  S
  406 tcgatctacgacatcgacttcgtgtacctcgaaggtgtggagcgc 450
      S  I  Y  D  I  D  F  V  Y  L  E  G  V  E  R
  451 aatccggtcggtgcaggtctcaaagtcatcgaccacctgacccac 495
      N  P  V  G  A  G  L  K  V  I  D  H  L  T  H
  496 aacgtctatcgcggccgcatggtctactgggccaacttctacgag 540
      N  V  Y  R  G  R  M  V  Y  W  A  N  F  Y  E
  541 aaattgttcaacttccgtgaagcgcgttacttcgatatcaagggc 585
      K  L  F  N  F  R  E  A  R  Y  F  D  I  K  G
  586 gagtacaccggcctgacttccaaggccatgagtgcgccggacggc 630
      E  Y  T  G  L  T  S  K  A  M  S  A  P  D  G
  631 atgatccgcatcccgctgaacgaagagtcgtccaagggcgcgggg 675
      M  I  R  I  P  L  N  E  S  S  K  G  A  G
  676 cagatcgaagagttcctgatgcagttcaacggcgaaggcatccag 720
      Q  I  E  E  F  L  M  Q  F  N  G  E  G  I  Q
  721 cacgtggcgttcctcaccgacgacctggtcaagacctgggacgcg 765
      H  V  A  F  L  T  D  D  L  V  K  T  W  D  A
  766 ttgaagaaaatcggcatgcgcttcatgaccgcgccgccagacact 810
      L  K  K  I  G  M  R  F  M  T  A  P  P  D  T
  811 tattacgaaatgctcgaaggccgcctgcctgaccacggcgagccg 855
      Y  Y  E  M  L  E  G  R  L  P  D  H  G  E  P
  856 gtggatcaactgcaggcacgcggtatcctgctggacggatcttcc 900
      V  D  Q  L  Q  A  R  G  I  L  L  D  G  S  S
  901 gtggaaggcgacaaacgcctgctgctgcagatcttctcggaaacc 945
      V  E  G  D  K  R  L  L  L  Q  I  F  S  E  T
  946 ctgatgggcccggtgttcttcgaattcatccagcgcaagggcgac 990
      L  M  G  P  V  F  F  E  F  I  Q  R  K  G  D
  991 gatgggtttggcgagtggaacttcaaggcgctgttcgagtccatc 1035
      D  G  F  G  E  W  N  F  K  A  L  F  E  S  I      <- W336
 1036 gaacgtgaccaggtcgtcgtggtgtattgaccgccgattaa 1077
      E  R  D  Q  V  R  R  G  V  L  T  A  D  *
```

2E6

1C5

6H11

Polyclonal

SEQUENCE LISTING

<160> NUMBER OF SEQ ID NOS: 5

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgaaacatc accatcacca tcaccatatg cag                                    33

<210> SEQ ID NO 2
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1074)

<400> SEQUENCE: 2 atg gca gat cta tac gaa aac cca atg ggc ctg atg ggc ttt gaa ttc        48
Met Ala Asp Leu Tyr Glu Asn Pro Met Gly Leu Met Gly Phe Glu Phe
1               5                   10                  15 atc gaa ttc gca tcg ccg acg ccg ggt acc ctg gag ccg atc ttc gag        96
Ile Glu Phe Ala Ser Pro Thr Pro Gly Thr Leu Glu Pro Ile Phe Glu
                20                  25                  30 atc atg ggc ttc acc aaa gtc gcg acc cac cgt tcc aag aac gtg cac       144
Ile Met Gly Phe Thr Lys Val Ala Thr His Arg Ser Lys Asn Val His
            35                  40                  45 ctg tac cgc cag ggc gag atc aac ctg atc ctc aac aac gag ccc aac       192
Leu Tyr Arg Gln Gly Glu Ile Asn Leu Ile Leu Asn Asn Glu Pro Asn
        50                  55                  60 agc atc gcc tcc tac ttt gcg gcc gaa cac ggc ccg tcg gtg tgc ggc       240
Ser Ile Ala Ser Tyr Phe Ala Ala Glu His Gly Pro Ser Val Cys Gly
65                  70                  75                  80 atg gcg ttc cgc gtg aag gac tcg caa aag gcc tac aac cgc gcc ctg       288
Met Ala Phe Arg Val Lys Asp Ser Gln Lys Ala Tyr Asn Arg Ala Leu
                85                  90                  95 gaa ctc ggc gcc cag ccg atc cat att gac acc ggg ccg atg gaa ttg       336
Glu Leu Gly Ala Gln Pro Ile His Ile Asp Thr Gly Pro Met Glu Leu
            100                 105                 110 aac ctg ccg gcg atc aag ggc atc ggc ggc gcg ccg ttg tac ctg atc       384
Asn Leu Pro Ala Ile Lys Gly Ile Gly Gly Ala Pro Leu Tyr Leu Ile
        115                 120                 125

```
gac cgt ttc ggc gaa ggc agc tcg atc tac gac atc gac ttc gtg tac     432
Asp Arg Phe Gly Glu Gly Ser Ser Ile Tyr Asp Ile Asp Phe Val Tyr
    130                 135                 140 ctc gaa ggt gtg gag cgc aat ccg gtc ggt gca ggt ctc aaa gtc atc     480
Leu Glu Gly Val Glu Arg Asn Pro Val Gly Ala Gly Leu Lys Val Ile
145                 150                 155                 160 gac cac ctg acc cac aac gtc tat cgc ggc cgc atg gtc tac tgg gcc     528
Asp His Leu Thr His Asn Val Tyr Arg Gly Arg Met Val Tyr Trp Ala
                165                 170                 175 aac ttc tac gag aaa ttg ttc aac ttc cgt gaa gcg cgt tac ttc gat     576
Asn Phe Tyr Glu Lys Leu Phe Asn Phe Arg Glu Ala Arg Tyr Phe Asp
            180                 185                 190 atc aag ggc gag tac acc ggc ctg act tcc aag gcc atg agt gcg ccg     624
Ile Lys Gly Glu Tyr Thr Gly Leu Thr Ser Lys Ala Met Ser Ala Pro
        195                 200                 205 gac ggc atg atc cgc atc ccg ctg aac gaa gag tcg tcc aag ggc gcg     672
Asp Gly Met Ile Arg Ile Pro Leu Asn Glu Glu Ser Ser Lys Gly Ala
    210                 215                 220 ggg cag atc gaa gag ttc ctg atg cag ttc aac ggc gaa ggc atc cag     720
Gly Gln Ile Glu Glu Phe Leu Met Gln Phe Asn Gly Glu Gly Ile Gln
225                 230                 235                 240 cac gtg gcg ttc ctc acc gac gac ctg gtc aag acc tgg gac gcg ttg     768
His Val Ala Phe Leu Thr Asp Asp Leu Val Lys Thr Trp Asp Ala Leu
                245                 250                 255 aag aaa atc ggc atg cgc ttc atg acc gcg ccg cca gac act tat tac     816
Lys Lys Ile Gly Met Arg Phe Met Thr Ala Pro Pro Asp Thr Tyr Tyr
            260                 265                 270 gaa atg ctc gaa ggc cgc ctg cct gac cac ggc gag ccg gtg gat caa     864
Glu Met Leu Glu Gly Arg Leu Pro Asp His Gly Glu Pro Val Asp Gln
        275                 280                 285 ctg cag gca cgc ggt atc ctg ctg gac gga tct tcc gtg gaa ggc gac     912
Leu Gln Ala Arg Gly Ile Leu Leu Asp Gly Ser Ser Val Glu Gly Asp
    290                 295                 300 aaa cgc ctg ctg ctg cag atc ttc tcg gaa acc ctg atg ggc ccg gtg     960
Lys Arg Leu Leu Leu Gln Ile Phe Ser Glu Thr Leu Met Gly Pro Val
305                 310                 315                 320 ttc ttc gaa ttc atc cag cgc aag ggc gac gat ggg ttt ggc gag tgg    1008
Phe Phe Glu Phe Ile Gln Arg Lys Gly Asp Asp Gly Phe Gly Glu Trp
                325                 330                 335 aac ttc aag gcg ctg ttc gag tcc atc gaa cgt gac cag gtg cgt cgt    1056
Asn Phe Lys Ala Leu Phe Glu Ser Ile Glu Arg Asp Gln Val Arg Arg
            340                 345                 350 ggt gta ttg acc gcc gat taa                                        1077
Gly Val Leu Thr Ala Asp
        355

<210> SEQ ID NO 3
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45
```

```
Leu Tyr Arg Gln Gly Glu Ile Asn Leu Ile Leu Asn Asn Glu Pro Asn
     50                  55                  60

Ser Ile Ala Ser Tyr Phe Ala Ala Glu His Gly Pro Ser Val Cys Gly
 65                  70                  75                  80

Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
                180                 185                 190

Ile Lys Gly Glu Tyr Thr Gly Leu Thr Ser Lys Ala Met Ser Ala Pro
            195                 200                 205

Asp Gly Met Ile Arg Ile Pro Leu Asn Glu Glu Ser Ser Lys Gly Ala
            210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 4
<211> LENGTH: 358
<212> TYPE: PRT
<213> ORGANISM: Pseudomonas fluorescens

<400> SEQUENCE: 4

Met Ala Asp Leu Tyr Glu Asn Pro Met Gly Leu Met Gly Phe Glu Phe
 1               5                  10                  15

Ile Glu Phe Ala Ser Pro Thr Pro Gly Thr Leu Glu Pro Ile Phe Glu
                 20                  25                  30

Ile Met Gly Phe Thr Lys Val Ala Thr His Arg Ser Lys Asn Val His
             35                  40                  45

Leu Tyr Arg Gln Gly Glu Ile Asn Leu Ile Leu Asn Asn Glu Pro Asn
     50                  55                  60
```

```
Ser Ile Ala Ser Tyr Phe Ala Ala Glu His Gly Pro Ser Val Cys Gly
 65                  70                  75                  80

Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5
```

ANTIBODIES IMMUNOREACTIVE WITH MUTANT HYDROXYPENYLPYRUVATE DIOXYGENASE

BACKGROUND OF THE INVENTION

The hydroxyphenylpyruvate dioxygenases are enzymes which catalyze the reaction in which para-hydroxyphenylpyruvate (HPP) is transformed into homogentisate. This reaction takes place in the presence of iron and in the presence of oxygen (Crouch, N. P. et al., *Tetrahedron*, 53, 20, 6993-7010, 1997). It may be hypothesized that the HPPDs contain an active site which is capable of catalyzing this reaction, in which iron, the substrate and the molecule of oxygen link together.

Some molecules which inhibit this enzyme, and which bind to the enzyme in order to inhibit transformation of the HPP into homogentisate, are also known. Some of these molecules have been used as herbicides since inhibition of the reaction in plants leads to whitening of the leaves of the treated plants and to the death of the said plants (Pallett, K. E. et al. 1997 *Pestic. Sci.* 50 83-84). The herbicides for which HPPD is the target, and which are described in the state of the art, are, in particular, isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506,195), in particular sulcotrione, or else pyrazolinates.

In addition, the amino-acid sequence of hydroxyphenylpyruvate dioxygenase from *Pseudomonas* sp. P.J. 874 has been described (Ruetschi et al.: Eur. J. Biochem. 205, 459-466, 1992). At U.S. Pat. No. 6,268,549, a sequence of a gene of this type is described and that such a gene can, once incorporated into plant cells, produce an over-expression or an activation of HPPD in the plants giving to the latter an worthwhile tolerance to certain novel herbicides, such as those of the isoxazoles family or that of the triketones. The sequence can be of bacterial origin, such as especially the genus *Pseudomonas* or alternatively of plant origin, such as especially of monocotyledonous or dicotyledonous plants, especially of *Arabidopsis* or of Umbelliferae, such as, for example, the carrot (*Daucus carotta*). It can be isolated native or wild or possibly mutated artificially while at the same time fundamentally retaining a property of herbicidal tolerance against HPPD inhibitors, such as herbicides of the isoxazoles family or that of the triketones.

Also described at U.S. Pat. No. 6,245,968 is a mutant of such HPPD sequences. It is useful in the process of over expressing the sensitive enzyme so as to produce quantities of the target enzyme in the plant sufficient to have enough functional enzyme in spite of the presence of the inhibitor. The patent describes that by mutating the enzyme in the vicinity of its C-terminal part, it was possible to obtain functional (enzymatically active) HPPDs which were less sensitive to HPPD inhibitors, such that expression of these functional HPPDs in plants improves the tolerance of the plants to HPPD inhibitors. Mutants which are enzymatically active or functional retain a significant portion of HPPD catalytic activity, and in the case of plants transformed with the sequences, the mutated sequences should preferably retain sufficient HPPD activity to sustain the growth of the plant.

With this mutation an amino acid of the primary sequence is replaced with another amino acid. By aligning these known sequences, by using the customary means of the art, such as, for example, the method described by Thompson, J. D. et al, (CLUSTALW: improving the sensitivity of progressive multiple sequence alignment through sequence weighting, positions-specific gap penalties and weight matrix choice. *Nucleic Acids Research*, 22; 4673-4680, 1994), and accessing these computer programs for sequence alignment which include a wide variety of tools, and are accessible via the Internet, for example, the skilled person is able to define the sequence homologies in relation to a reference sequence and find the key amino acids or else define common regions, making it possible, for example to align the sequence and locate a referenced position and to define a C-terminal region and an N-terminal region on the basis of this reference sequence.

In the case of the present invention, the reference sequence is the *Pseudomonas* sequence, with all the definitions and indications of the positions of particular amino acids being made with respect to the primary *Pseudomonas* HPPD sequence, here SEQ ID NO: 4 (this is the sequence identified as sequence 31 of the '968 patent). That reference sequence is shown in FIG. 1 of the '968 patent and depicts an alignment of several HPPD sequences which are described in the state of the art; these sequences are aligned with respect to the *Pseudomonas* HPPD sequence as the reference sequence and comprise the HPPD sequences as described therein of *Streptomyces avermitilis* (Genebank SAV 11864), of *Daucus carota* (Genebank DCU87257), of *Arabidopsis thaliana* (Genebank AF047834), of *Zea mays* (Genbank NM001112312), of *Hordeum vulgare* (Genebank HVAJ693), of *Mycosphaerella graminicola* (Genebank AF038152), of *Coccicoides immitis* (Genebank COITRP) and of *Mus musculus* (Genebank MU54HD). This figure gives the numbering of the amino acids of the *Pseudomonas* sequence and also the amino acids which are common to these sequences, with these amino acids being designated by an asterisk. On the basis of such an alignment, it is straightforward, from the definition of the *Pseudomonas* amino acid by its position and its nature, to identify the position of the corresponding amino acid in another HPPD sequence (with the alignment of sequences of different plant, mammalian and bacterial origin demonstrating that this method of alignment, which is well known to a skilled person, can be generalized to any other sequence). An alignment of different HPPD sequences is also described at Maxwell et al. US Patent Publication 20030066102 and Patent Application WO97/49816. The C-terminal part of the HPPDs, which is where the active site of the enzyme is located, differs from its N-terminal part by a linking peptide which ensures the stability of the enzyme and its oligomerization (the *Pseudomonas* HPPD is a tetramer while the plant HPPDs are dimers). The linking peptide makes it possible to define the N-terminal end of the C-terminal part of the enzyme, with the said peptide being located between amino acids 145 and 157 in the case of *Pseudomonas*. The C-terminal part can therefore be defined as consisting of the sequence defined, on the one hand, by the linking peptide and, on the other hand, by the C-terminal end of the enzyme, with the mutation which is effected in the C-terminal part of the HPPD therefore being effected in the region which has thus been defined. Two amino acids, which are in positions 161 and 162 in the case of the *Pseudomonas* sequence (D=Asp161 and H=His162), will be noted in all sequences. With reference to the *Pseudomonas* HPPD, it is therefore possible to define the linking peptide which represents the N-terminal end of the C-terminal part of the HPPD as being located between approximately 5 and 15 amino acids upstream of the amino acid Asp161. The mutation of interest in the present invention is effected on amino acids being located with reference to the *Pseudomonas* sequence at position 336.

There is a need to identify antibodies that are immunoreactive with the mutant HPPD protein described above so that plants containing such mutated HPPD protein can be readily identified. Especially useful would be an antibody that immunoreacts with *Pseudomonas* HPPD and especially the mutant HPPD protein containing the mutation at residue 336 (glycine (gly or G) to tryptophan (trp or W)). A method that would avoid time-consuming lab steps would reduce costs, allowing for quick identification of the transgenic plants containing the mutant protein, aiding in breeding and selection. Furthermore, antibodies that are immunoreactive with such proteins could be useful in isolating and purifying the proteins.

All references cited are incorporated herein by reference. The instant application contains a Sequence Listing which has been submitted via EFS-Web and is hereby incorporated by reference in its entirety. Said ASCII copy, created on Oct. 22, 2009, is named 210004.txt, and is 12,549 bytes in size.

SUMMARY OF THE INVENTION

The invention is directed to hybridomas and the antibodies and fragments produced from the hybridomas, which are immunoreactive with the amino acid sequence of a mutant HPPD gene. The amino acid sequence is that which substitutes a glycine for tryptophan at residue 336 when compared to a wild-type HPPD polypeptide, and in one embodiment makes such substitution at position 336 of the *Pseudomonas fluorescens* A32 HPPD gene as is represented at SEQ ID NO: 4 and also with the corresponding mutations shown in FIG. 1 and is SEQ ID NO: 3. Use of the antibodies to identify plant cells having said amino acids and to isolate and purify same are also disclosed.

BRIEF DESCRIPTION OF THE DRAWINGS

FIG. 1 shows the His-tag used in isolating the sequence, which is the first 33 bases in bold (SEQ ID NO: 1) and the 1077 nucleotide sequence of the open reading frame of the HPPD mutant beginning at base pair 34 with the ATG start site (SEQ ID NO: 2) and the encoded amino acid sequence (SEQ ID NO: 3) set forth below. The mutation of glycine to tryptophan is in bold and underlined and corresponds with position 336 of the *Pseudomonas fluorescens* A32 HPPD (SEQ ID NO: 4).

DETAILED DESCRIPTION OF EMBODIMENTS OF THE INVENTION

Figure 2:
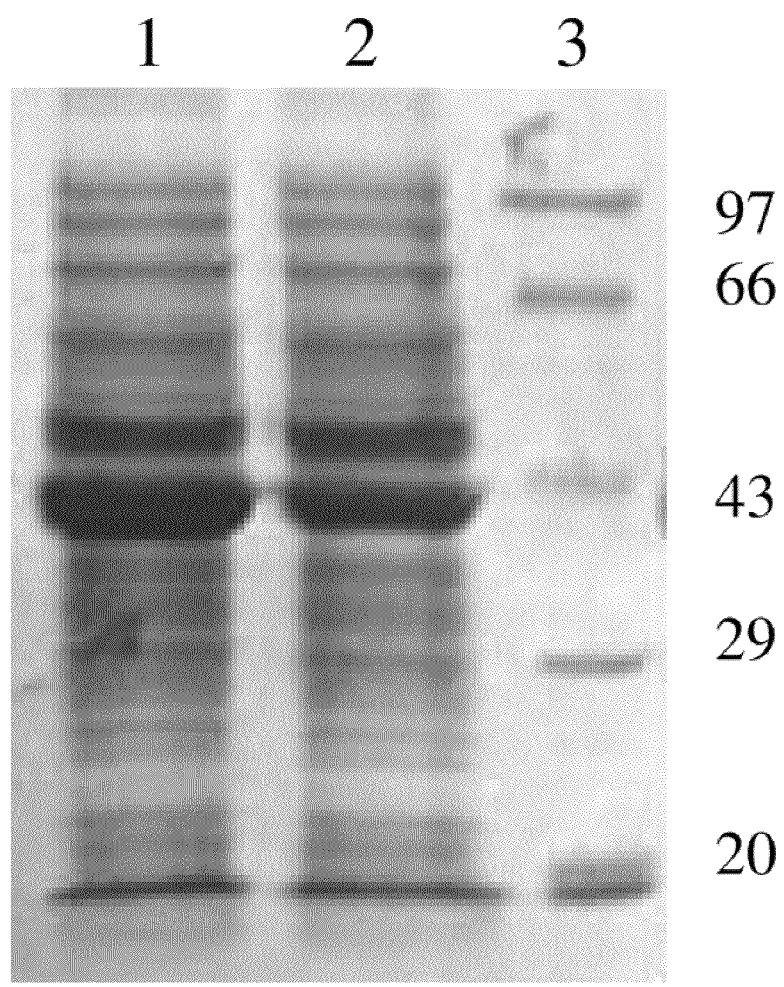
FIG. 2 is an SDS-PAGE gel of the mutant HPPD-expressed in *E. coli*. Lane 1 is supernatant of sonicate (soluble part), lane 2 is precipitate of sonicate (inclusion body) and lane 3 shows molecular weight standards.

Described here are hybridomas and antibodies and fragments of same, prepared from these hybridomas against a mutant hydroxyphenyl pyruvate dioxygenase (HPPD) enzyme. The monoclonal antibodies immunoreactive with and are useful to identify presence of the enzyme, and to isolate and purify the enzyme. Terms used herein employ their common definitions; for example, immunoreactive refers to reacting to particular antigens or haptens, and wild-type refers to the polypeptide as it occurs in nature. A mutant HPPD enzyme is one in which, compared to a wild-type HPPD, which in an embodiment can be the *Pseudomonas* HPPD, there is a mutation of the amino acid of the enzyme aligned with position 336 of that HPPD protein as can be readily determined, as described supra. See also, for example, GenBank Accession No. DQ459070, which aligns with the mutant except at this particular position. As the mutant is shown in FIG. 1, the mutation occurs at position 336 (excluding the His-tag) As shown in the examples below, the monoclonal antibody is immunoreactive to a HPPD protein containing tryptophan at residue 336 of the HPPD of *P. fluorescens*. This sequence is shown in FIG. 1 with the mutation position bolded and underlined and is SEQ ID NO: 3. Reference to the numbering of residues of the HPPD amino acid is used in examples here not to limit the invention, but to facilitate comparison of HPPD sequences from sources from various sources. As used herein when referring to the "antibody" or "polyclonal antibody" or "monoclonal antibody" (MAb) of the invention is meant an antibody or fragment of same that is immunoreactive with a *Pseudomonas* HPPD amino acid sequence having said mutation.

An antibody (or an immunoglobulin) is a protein synthesized by an animal in response to the presence of a foreign substance that is called an antigen. Each antibody molecule has a unique structure that enables it to bind specifically to its corresponding antigen, but all antibodies have the same overall structure. An antibody molecule is composed of two distinct regions. One is a constant region and the other is a variable region that gives an antibody the specificity to a vast variety of different antigens.

Five major classes of antibodies are IgM, IgD, IgG, IgA, and IgE. IgG is the most abundant class. IgG, as an example, has a molecular weight of 150 kDa and is composed of two different types of polypeptide chains: one is the heavy chain (50 kDa) and the other is the light chain (25 kDa). Each IgG molecule has two heavy chains and two light chains linked by disulfide bonds. Variable regions of the heavy ($V_H$) and light ($V_L$) chains together function as the variable region of the antibody and give the antibody the ability to bind a specific antigen.

In the amino acid sequences discussed here, the standard single letter or three letter nomenclature is used. All peptide structures represented in the following description are shown in conventional format in which the amino group at the N-terminus appears to the left and the carboxyl group at the C-terminus at the right Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr,T), tryptophan (Trp;W), tyrosine (Tyr;Y), and valine (Val;V). An "X" may be used when the amino acid residue is unknown and parentheses designate that an unambiguous assignment is not possible and the amino acid designation within the parentheses is the most probable estimate based on known information.

Deoxyribonucleic acid (DNA) is a polymer comprising four mononucleotide units, DAMP (2'-Deoxyadenosine-5- monophosphate), dGMP (2'-Deoxyguanosine-5-monophosphate), dCMP (2'-Deoxycytosine-5-monophosphate) and dTMP (2'-Deoxycytosine-5-monophosphate) linked in various sequences by 3',5'-phosphodiester bridges. The structural DNA consists of multiple nucleotide triplets called "codons" which code for the amino acids. The codons correspond to the various amino acids as follows: Arg (CGA, CGC, CGG, CGT, AGA, AGG); Leu (CTA, CTC, CTG, CTT, TTA, TTG); Ser (TCA, TCC, TCG, TCT, AGC, AGT); Thr (ACA, ACC, ACG, ACT); Pro (CCA, CCC, CCG, CCT); Ala (GCA, GCC, GCG, GCT); Gly (GGA, GGC, GGG, GGT); Ile (ATA, ATC, ATT); Val (GTA, GTC, GTG, GTT); Lys (AAA, AAG); Asn (AAC, AAT); Gln (GAA, CAG); His (CAC, CAT); Glu (GAA, GAG); Asp (GAC, GAT); Tyr (TAC, TAT); Cys (TGC, TGT); Phe (TTC, TTT); Met (ATG); and Trp (UGG). Moreover, due to the redundancy of the genetic code (i.e., more than one codon for all but two amino acids), there are many possible DNA sequences which may code for a particular amino acid sequence.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane, *Antibodies: A Laboratory Manual*, Chapter 5, p. 76, Cold Spring Harbor Laboratory, New York (1988); or Coligan (1991) *Current Protocols in Immunology* Wiley/Greene, N.Y.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual CSH Press*; Goding (1986) *Monoclonal Antibodies: Principles and Practice* (2d ed.) Academic Press, New York, N.Y.; and particularly in Kohler and Milstein (1975) *Nature* 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. Clearly many such different methods and variations are available to one skilled in the art.

The use of somatic hybrid cell lines as sources of antibody to individual antigens generally dates from the work of Kohler and Milstein (1975), supra. The antibodies produced are quite different than those recovered from antiserum from conventionally immunized animals. Each hybrid cell line synthesizes a homogenous immunoglobulin that represents but one of the myriad of types of antibodies that an animal can synthesize in response to an antigen in vivo. Since each immunoglobulin-producing clone is characterized by the single type of antibody it produces, the term monoclonal antibody has been adopted. The advantages of monoclonal antibodies are numerous; they can be obtained in large supply; the preparation is homogenous with respect to antigen reactivity and remains so over time.

The principle of hybridoma/monoclonal technology is predicated on the observation that when two somatic cells are fused the resultant hybrid displays characteristics of both of the parent cell types. In the case of monoclonal antibody production, the ability to synthesize the particular antibody is derived from an immunocompetent cell (usually a spleen cell) taken from an immunized donor animal, whereas the ability to continuously divide in cell culture is contributed by the other fusion partner, a tumor cell line (often a myeloma). Early fusions were complicated by the fact that myeloma cell line also produced a monoclonal antibody; thus the hybrid often produced two types of monoclonal antibody, one of myeloma origin and the other directed by the genetic information of the immunocompetent cell. Subsequently, tumor cells lines incapable of producing their own monoclonal have been used, e.g., SP2/0-Ag14 or X63-Ag8.653, thereby simplifying the analysis of the resultant fusion products.

Another technical consideration involves the rationale for selecting the successful fusion events (hybrid cells) from the two types of parental cells. Routinely a million or more cells of each type are used in the fusion protocol, and since fusion does not occur with 100% frequency, the job of trying to recover fusion products from the high background of unfused or self-fused parents can be formidable. As mentioned hybridomas are formed by the fusion of short-lived antibody producing (spleen) cells and long-lived myeloma cells. The desired result is a long-lived cell line which produces antibody. Since the spleen cells have a finite life span in culture one can simply wait an appropriate period for all the nonfused or self-fused spleen cells to die; however one must still recover from the resultant population the long-lived antibody producing cells from the long-lived antibody non-producing cells. A popular means for selection hybrid cells is the so-called HAT-selection system. This system involves the use of the enzyme hypoxanthine-guanine-phosphoribosyl transferase (HGPRT). This enzyme functions in the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates on the same enzyme but in the opposite sense in that HGPRT positive cells are selected is described by J. W. Littlefield (*Science*, 145: 709 (1964)). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvageable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

In a hybrid system which can be used for selection in accordance with the invention, the myeloma cells are resistant to azaguanine and susceptible to aminopterin, that is, they are HGPRT negative. Thus, they will die in the presence of aminopterin. The antibody producing cells are HGPRT positive. By fusing the cells and growing them in HAT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT medium, systems are produced in which the myeloma cells and antibody producing cells can grow long enough to produce hybrid cells but in which only the hybrid cells can survive and proliferate. After selection each hybridoma clone is then screened for the ability to produce the particular antibody of interest.

A mutant HPPD protein was purified and used as the antigen in the preparation of the HPPD-specific monoclonal antibody. In one embodiment, a preparation process is characterized in that: a) an extract is made from E. coli expressing the mutant HPPD protein, preserved at low temperature by grinding, centrifugation and filtration, b) the extract obtained is enriched in HPPD protein by precipitation in an appropriate solvent, centrifugation and solubilisation of the precipitate obtained in a buffer solution, c) the active protein thus obtained is purified by chromatography and if desired, d) the hybridomas and monoclonal antibodies are prepared from an antigen solution obtained from one of the preparations obtained in paragraphs a), b), and c) above, e) the hybridomas are screened and the monoclonal antibody or antibodies directed specifically against the mutant HPPD are selected.

In describing the above is not meant to limit the production of the antibodies of the invention to such precise systems; as further methods of such antibody production are developed and optimized they are well within the scope of the invention.

The monoclonal antibodies so isolated can be used in a variety of ways. As demonstrated below, the antibodies can distinguish between plant tissue containing the mutated *Pseudomonas* HPPD protein, and those which do not contain this protein. Thus the antibodies can be used to identify those plant cells, tissue and plants which contain the HPPD protein, thus allowing for selection of such plants without destroying the plant nor requiring extensive field tests.

Kits useful with the invention may take any of a variety of forms and in general provide for obtaining an amino acid containing sample from plant tissue, a support having affixed to it the antibody of the invention capable of forming a binary complex with the HPPD which may be present in the sample, and a binary complex detecting means. The specifics of the kit beyond employing the antibody or fragment immunoreactive properties of the invention are not critical. The method or means of obtaining the amino acid containing sample is not critical, and can take any form, as long as a plant sample is obtained; the detecting means likewise can take any of a myriad of forms, as is well appreciated by one skilled in the art. Detecting means have been used for some time, and can include, for example, biotin, a fluorescent dye, a radio isotope or an enzyme.

In one embodiment, for example, the monoclonal antibody may be applied to a support structure, such as a test strip. By way of example without intending to limit the application of the invention, the antibody may be used with an immunostrip. One antibody is conjugated to a gold particle and applied to a fiber pad. A second antibody is striped as a line onto a membrane. A strip is assembled in such a way as that a sample pad is placed into the sample extract and the antigen is wicked up the strip, coming in contact with the conjugated MAb and later with the striped MAb. The striped MAb "captures" the antigen-conjugate complex forming a colored line. If no antigen is present, no line forms. A kit would comprise materials required to perform a test for mutant HPPD.

In the event precise determinations for presence of the mutant are required, other tests are well known to one skilled in the art. By way of example, without limitation, a Western Blot analysis is among the type of test that may be employed. A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was either $^{32}$P labeled (radioactive) or non-radio labeled and washed in an SDS solution. In the Western analysis, instead of isolating DNA, the protein of interest is extracted and separated on an acrylamide gel. The protein is then blotted onto a membrane and treated with a labeling substance. See Towbin et al, (1979) "Electrophoretic transfer of proteins from polyacrylamide gels to nitrocellulose sheets: procedure and some applications" *Proc Natl Acad Sci USA* 76(9): 4350-4354; Renart et al (1979). "Transfer of proteins from gels to diazobenzyloxymethyl-paper and detection with antisera: a method for studying antibody specificity and antigen structure" *Proc Natl Acad Sci USA* 76(7): 3116-3120.

Another way the MAbs can be used is in a double antibody sandwich ELISA. The antigen-antibody interactions are similar to those of the immunostrip but take place in the wells of a polystyrene plate.

The antibodies may also be used in purifying and isolating the HPPD protein. For example, samples containing proteins may be passed through a chromatography column containing the monoclonal antibodies of the invention such that the proteins bind to and are isolated from other proteins in the sample.

Clearly the antibodies of the invention may be employed in a variety of uses, a few of which are exemplified here, and which are known to those skilled in the art.

The following are presented by way of illustration and are not intended to limit the scope of the invention.

EXPERIMENTAL

Isolation of his-tagged HPPD Protein

Isolation of the HPPD protein expressed in bacteria used standard protocols as provided by Qiagen, Inc. (The *QIAexpressionist*™: A handbook for high-level expression and purification of 6xHis-tagged (SEQ ID NO: 5) proteins. Fifth Edition, 2003)

The protocol used in summarized as follows.

Protein Expression

1. The *E. coli* strain was cultured in 1L LB media for 4 hours and then induced by 0.5 mmol/L IPTG for 5 hours at 28° C.

2. The cells were harvested by centrifugation and disrupted by sonication.

3. The target protein was largely expressed in soluble form (as shown in FIG. 2; lane 1 showing supernatant of sonicate (soluble part), lane 2 showing precipitate of sonicate (inclusion body) and lane 3 is standard molecular weights.).

Protein Purification

4. The cells paste was suspended in LEW Buffer and disrupted with sonication on ice. The sonicate was centrifuged at high speed for 20 min. The supernatant was collected and applied to High Affinity Ni-IDA Resin (Cat. No L00223) to purify the fusion protein (as shown in FIG. 2).

5. Dialysis the eluate against 1×PBS.

Figure 3:
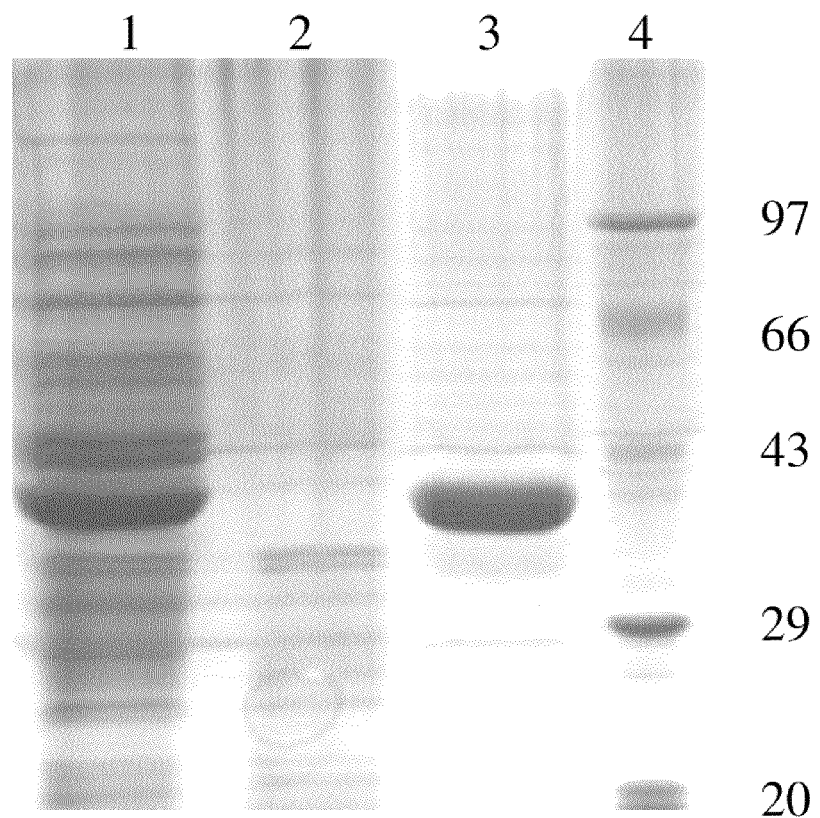
FIG. 3 is an SDS-PAGE gel of mutant HPPD target protein purification profile by Ni-IDS affinity chromatography. Lane 1 is supernatant of sonicate, lane 2 is wash, lane 3 is eluate and lane 4 molecular weight standards.
Figure 4A:
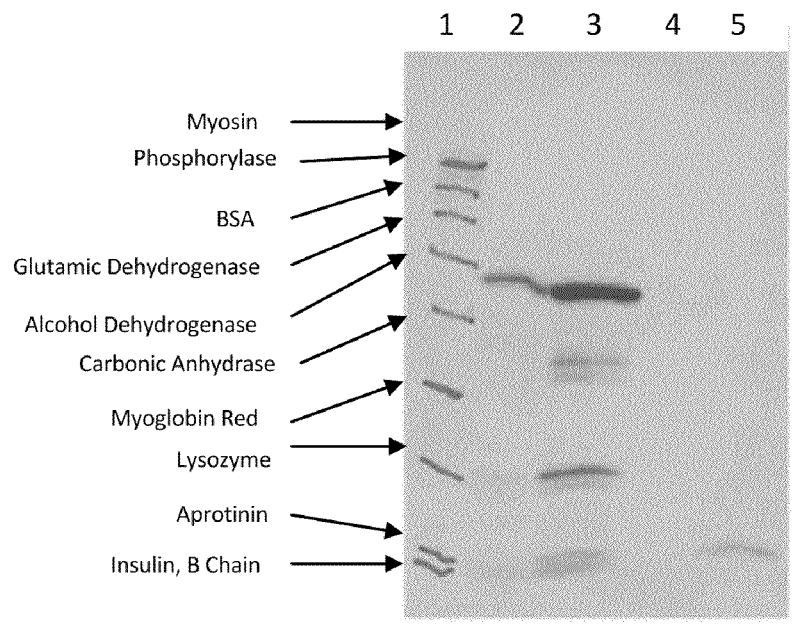
FIG. 4A is a Western blot using monoclonal antibody 2E6; 4B is using monoclonal antibody 1C5; 4C is using monoclonal antibody 6H11; and 4D is using the polyclonal antiserum. Lane 1 is the molecular weight standards, lane 2 is cotyledon extract of a transgenic plant expressing HPPD protein, lane 3 is a non-transformed soybean plant with added purified HPPD protein (lane 4 is empty) and lane 5 is cotyledon extract of a non-transformed soybean plant.
Figure 4B:
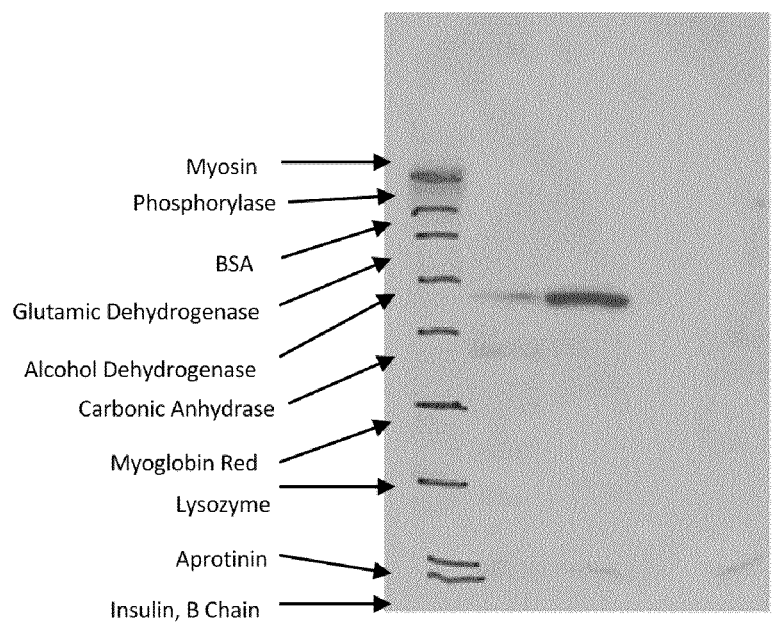
Figure 4C:
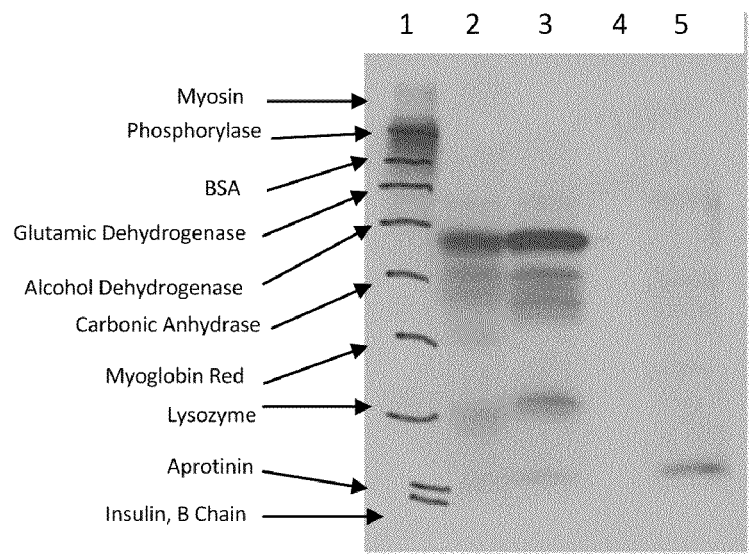
Figure 4D:
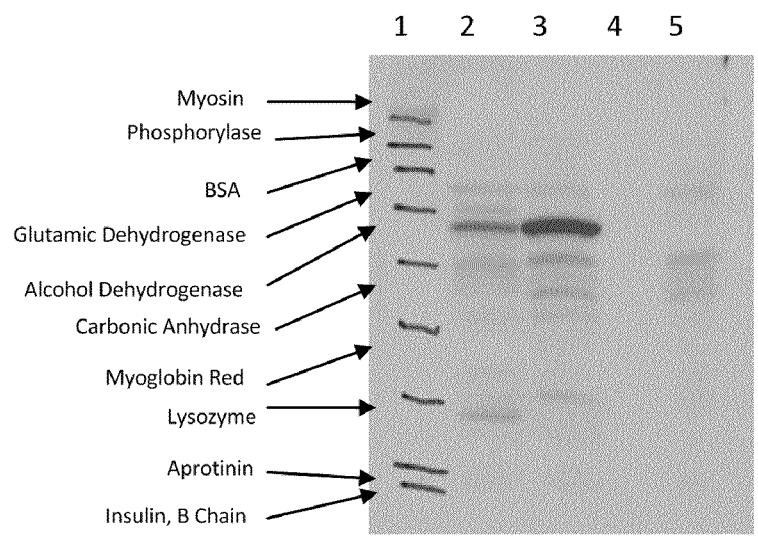

Results of SDS-PAGE of mutant HPPD target protein purification profile by Ni-IDA Affinity are shown in FIG. 3. Lane 1 is supernatant of sonicate, lane 2 wash, lane 3 eluate, lane 4 shows standard molecular weights.

Production of Antibodies

BALB/c mice were primed and boosted three to four times with purified bacterially expressed 6×His-HPPD every two to four weeks. Complete and incomplete Freund's Adjuvant from Sigma were used for the priming and the boostings respectively. After two boosts, serum titers were monitored by ELISA. Once the titers were high enough, splenocytes were harvested from the immunized mice and fused with myeloma cells (P3/NSI/1-Ag4-1) using PEG1500 as a fusion agent. The resulting cell fusion products were diluted in hybridoma medium and seeded into 96-well tissue culture plates. After one day, HAT medium was added to the hybridoma cultures. Since then the medium had been changed every three or four days as necessary with HT medium. After ten to fourteen days of culture with selection, screening was initiated by ELISA.

Antibodies were screened against with purified 6×His-HPPD and 6×His-KLH ('6×His' disclosed as SEQ ID NO: 5). Ninety-six well Nunc Maxi-sorp Immunoplates™ (Nunc # 446612, Roskilde, Denmark) were coated by adding 50 µl per well of solution of HPPD and by adding 50 µl per well of 0.5 µg/ml solution of 6×His-KLH ('6×His' disclosed as SEQ ID NO: 5) in coating buffer (BupH.™. Carbonate-Bicarbonate Buffer, Pierce # 28382, Rockford, Ill.) for one hour at room temperature. The coating buffer was removed and the plate was blocked by adding 250 µl per well of blocking buffer (1% Blocker, TM. BSA, Pierce # 37525, in PBS) for two hours at room temperature. 50 µl of hybridoma supernatant were added into the wells and incubated for one hour at room temperature. Wells were then washed four times with PBS/Tween 20. 50 µl of diluted (1:7,000) HRP-conjugated goat anti-mouse Ig (Southern Biotech #1010-05) was added into the wells and incubated for one hour at room temperature. The wells were washed five times with PBS/Tween 20. Anti-HPPD antibodies were detected by adding 50 µl per well of TMB (tetramethyl benzidine) solution (ImmunoPure®. TMB Substrate Kit, Pierce #34021) for 5 to 10 minutes. Plates were read spectorphotometrically at 405 nm using a microplate reader (Molecular Devices, Sunnyvale, Calif.).

Following the screenings of fusion products by ELISA, antibodies showing specific binding to HPPD were selected.

ELISA Screening

Monoclonal antibodies derived from hybridomas produced against HPPD were screened using an indirect double antibody sandwich (DAS) ELISA format. Briefly, plates were coated with a polyclonal antibody specific for HPPD. Buffer spiked with varying concentrations of HPPD, extracts of non-GMO soybean (Jack), and HPPD soybean were then incubated in the plate overnight. The plates were then incubated with HPPD specific monoclonal antibodies and then detected with alkaline phosphatase labeled rabbit anti mouse IgG. Monoclonal antibodies showing specificity for HPPD were chosen for further study. Nine antibodies designated 1C5, 2E6, 3C6, 5E9, 6H11, 7A7, 7F10, 8E7, and 12H1 were selected finally for their assay development. Results of one such screening is shown below.

The designation "PA056R@ 2 ug/ml" refers to the polyclonal HPPD antibody which was coated on the plate at 2 µg/ml. The category "HPPD µg/ml" refers to a standard curve made up from HPPD that was expressed in *E. coli* and purified.

Colorimetric response was recorded as optical density (OD) by an ELISA plate reader at a wavelength of 405 nM. This particular assay was read after 60 minutes of substrate development. After further screening, MAbs 1C5, 2E6, and 6H11 proved to have the greatest utility for detecting HPPD.

| HPPD Hybridoma Screen PA056R@ 2 ug/ml 60 min | | | | | | | | |
|---|---|---|---|---|---|---|---|---|
| HPPD µg/ml | 1C5 | 2E6 | 3C6 | 5E9 | 6H11 | 7A7 | 7F10 | 8E7 |
| 1 | ND | ND | 1.743 | 1.623 | ND | ND | 1.412 | ND |
| 0.250 | 0.732 | 1.149 | 1.194 | 0.980 | 0.969 | 1.473 | 0.785 | 0.726 |
| 0.063 | 0.369 | 0.679 | 0.671 | 0.441 | 0.527 | 0.800 | 0.491 | 0.291 |
| 0.016 | 0.214 | 0.391 | 0.314 | 0.155 | 0.268 | 0.414 | 0.196 | 0.148 |
| 0.004 | 0.143 | 0.251 | ND | ND | 0.173 | 0.248 | ND | 0.104 |
| Jack-L | 0.125 | 0.189 | 0.055 | 0.059 | 0.147 | 0.188 | 0.065 | 0.092 |
| FG74-L | 0.354 | 0.435 | 0.317 | 0.115 | 0.413 | 0.422 | 0.101 | 0.210 |

A deposit of hybridomas containing the antibodies of the invention is deposited with the ATCC which includes deposit number PTA-10312 hybridoma identified as 1C5; PTA-10313 hybridoma identified as 2E6; and PTA-10314 hybridoma identified as 6H11with the American Type Culture Collection (ATCC), 10801 University Boulevard, Manassas, Va. 20110-2209 USA. The hybridomas were deposited with the ATCC on Aug. 28, 2009. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent Western Blot Analysis of Selected Antibodies Specificity of the reactivity of the antibodies was confirmed by Western Blot Assay. See FIG. 4A-D. Extracts are obtained from soybean plant not transformed with HPPD (referred to as "Jack"—see Lane 5 of the gels in FIGS. 4A-D); as well as lines transformed with HPPD (Lane 2 of the gels of FIGS. 4A-D). Such lines were transformed by particle gun bombardment. (Described generally at Klein, T. M., Arentzen, R., Lewis, P. A. and Fitzpatrick-McElligott, S. (1992) Transformation of microbes, plants and animals by particle bombardment. *Biotechnology* (N Y) 10, 286-291) with the mutant HPPD gene and also with a double mutant EPSPS glyphosate resistant gene to create a soybean line (See sequence identifier 3 in U.S. Pat. Nos. 6,566,587 and 6,040, 497). (Lane 1 is molecular weight standards as indicated and having SeeBlue®Plus2 pre-stained marker from Invitrogen, #LC5929 with myosin, phosphorylase, BSA, glutamic dehydrogenase, alcohol dehydrogenase, carbonic anhydrase, myoglobin, lysozyme, aprotinin and insulin, B chain.)

Purified HPPD protein was also added to a non-transgenic soybean (see Lane 3 of the gels in FIGS. 4A-4D). Extract from the identified plants were separated by sodium dodecyl sulfate-polyacrylamide gel electrophoresis (SDS-PAGE) under reducing conditions, blotted onto nitrocellulose membrane and probed with the monoclonal antibody 2E6 (FIG. 4A) 1C5 (FIG. 4B), 6H11 (FIG. 4C) or polyclonal (FIG. 4D. In general, 8-16% BioRad Ready Gel is used in Bio-Rad Mini Protean 3 apparatus at 15 mA/gel until the samples are completely in gel, and then at 30 mA/gel. The electrophoresed proteins in the gels are transferred to PVDF membrane. Detection of immunoreactive proteins is performed using the Zymed Western Blot Kit (#96-9045).

A protein with an apparent molecular weight of 40 kD was identified by SDS-PAGE and matches the predicted molecular weight of the mutant HPPD protein sequence. The MAbs 1E6, 1C5 and 6H11 are specific for the HPPD in soybean in a similar fashion when purified HPPD is added to non-transgenic plant extract. Bands below the major band are degradation products from the full length protein. This is deduced because they are only detected in extracts containing HPPD and not in the non-transgenic extract. The degradation products are detected somewhat differently by the different monoclonals, as is to be expected since each recognizes a different epitope on the HPPD mutant protein molecule. As is demonstrated in the results, specifically lane 5 of the Westerns in FIG. 4A-D, endogenous non-mutant plant HPPD is not detected by the monoclonals, thus providing the ability to detect presence of the mutant Pseudomonas HPPD using the monoclonal antibodies.

What is claimed is:

1. An antibody or fragment thereof immunoreactive with a polypeptide with the amino acid sequence of SEQ ID NO:3 wherein said antibody is produced by a hybridoma selected from the group consisting of IC5 deposited with the ATCC under the accession number PTA-10312; 2E6 deposited with the ATCC under the accession number PTA-10313 and 6H11 deposited with the ATCC under the accession number PTA-10314.

2. An antibody produced by a hybridoma selected from the group consisting of IC5 deposited with the ATCC under the accession number PTA-10312; 2E6 deposited with the ATCC under the accession number PTA-10313 and 6H11 deposited with the ATCC under the accession number PTA-10314.

3. A method of detecting the presence of the polypeptide with the amino acid sequence of SEQ ID NO:3 in a composition, said method comprising contacting said composition with an antibody of claim1 and determining whether said antibody is immunoreactive with any the polypeptides present in said composition.

4. A kit for detecting the presence of the polypeptide with the amino acid sequence of SEQ ID NO:3 in a composition, said kit comprising an antibody of claim 1 and a detection agent.

* * * * *